US00PP16619P2

(12) United States Plant Patent
den Engelsen

(10) Patent No.: US PP16,619 P2
(45) Date of Patent: Jun. 6, 2006

(54) ***GENTIANA* PLANT NAMED 'BLUE ROCK'**

(50) Latin Name: *Gentiana pyrimidales*
Varietal Denomination: Blue Rock

(75) Inventor: Marcel den Engelsen, Someren (NL)

(73) Assignee: Vaste Planten Kwekerij de Leeuw Ploegstraat B.V., Someren (NL)

( * ) Notice: Subject to any disclaimer, the term of this patent is extended or adjusted under 35 U.S.C. 154(b) by 101 days.

(21) Appl. No.: 11/079,434

(22) Filed: Mar. 14, 2005

(51) Int. Cl.
*A01H 5/00* (2006.01)

(52) U.S. Cl. ..... Plt./263
(58) Field of Classification Search ..... Plt./263
See application file for complete search history.

*Primary Examiner*—Anne Marie Grunberg
(74) *Attorney, Agent, or Firm*—Penny J. Aguirre

(57) ABSTRACT

A new cultivar of Gentian, *Gentiana pyrimidales* 'Blue Rock', characterized by its light blue flowers borne on thick, strong stems combined with a late blooming season and a plant habit that is compact, short and uniform.

2 Drawing Sheets

Botanical classification: *Gentiana pyrimidales*.
Varietal denomination: 'Blue Rock'.

BACKGROUND OF THE INVENTION

The present invention relates to a new and distinct cultivar of *Gentiana pyrimidales* and will be referred to hereafter by its cultivar name, 'Blue Rock'. 'Blue Rock' represents a new Gentian, an herbaceous perennial grown for landscape use.

The inventor discovered the new cultivar, 'Blue Rock', as a naturally occurring whole plant mutation in a nursery plot of *Gentiana pyrimidales* 'Diana' (not patented) in Someren, The Netherlands in September of 2003.

The new cultivar 'Blue Rock' was selected as unique for its lighter blue colored flowers and a later flowering season in comparison to the parent plant 'Diana'.

Asexual reproduction of the new cultivar was first accomplished by in vitro propagation in Someren, The Netherlands in October of 2004. It has been determined by propagation both by stem cuttings and tissue culture that the characteristics of the new cultivar are stable and are reproduced true to type in successive generations.

SUMMARY OF THE INVENTION

The following traits have been repeatedly observed and represent the characteristics of a one year-old plant of the new cultivar after observing plants grown outdoors in a 13 cm pot Someren, The Netherlands. These attributes in combination distinguish 'Blue Rock' from 'Diana' and all other varieties of Gentians known to the inventor.

1. Light blue colored flowers. The parent plant, 'Diana' has darker colored blue flowers.
2. Late season bloomer, blooming from mid August to mid October. The parent plant, 'Diana' has an earlier blooming season.
3. Flowers are borne on upright, strong stems.
4. Plant habit is compact and uniform.

BRIEF DESCRIPTION OF THE PHOTOGRAPHS

The plants and plant parts in the photographs depict a one year-old plant of 'Blue Rock' as grown outdoors in 13 cm containers in Someren, The Netherlands.

The photograph on the first sheet provides an overall view of the new Gentian in bloom.

The photograph on the top of the second sheet is a close-up view of the flowers of 'Blue Rock' and the photograph on the bottom of the second sheet is a close-up view of a leaf of 'Blue Rock'.

The colors in the photographs are as close as possible with the photographic and printing technology utilized. The color values cited in the detailed botanical description accurately describe the color of the new Gentian.

DETAILED BOTANICAL DESCRIPTION

The following is a detailed description of one year-old plants the new cultivar grown outdoors in 13 cm containers in Someren, The Netherlands under natural light with average day temperatures ranging from 13° C. to 25° C. and average night temperatures ranging from 4° C. to 14° C. The phenotype of the new cultivar may vary with variations in environmental, climatic, and cultural conditions, as it has not been tested under all possible environmental conditions. The color determination is in accordance with the 2001 R.H.S. Colour Chart of the Royal Horticultural Society, London, England, except where general color terms of ordinary dictionary significance are used.

Botanical classification: 'Blue Rock' is a cultivar of *Gentiana pyrimidales*.

Parentage: Naturally occurring whole plant mutation derived from a branch of *Gentiana pyrimidales*, 'Diana'.

General description:

*Blooming period*.—Continuously from mid August to Mid October in The Netherlands.

*Plant type*.—Herbaceous perennial.

*Plant habit*.—Clump-forming, upright, compact, uniform.

*Growth rate*.—Moderate to slow growth rate.

*Height and spread*.—Average of 17 cm in height, 14 cm in spread.

*Hardiness*.—Hardy to at least U.S.D.A. Zone 6.

*Culture*.—Prefers humus-rich, moist but well-drained soils in partial shade or full sun in areas where summers are cool with sufficient moisture.

*Diseases and pests*.—No unique susceptibility or resistance to diseases or pests known to affect *Gentiana* has been observed for 'Blue Rock'.

*Root description*.—Fine.

Growth and propagation:

*Propagation*.—Stem cuttings and tissue culture.

*Root initiation*.—Roots appear on cuttings in about 10 days when grown at about 25° C. in a greenhouse without supplemental lighting during the summer months.

*Root development*.—Roots fully develop in a 13 cm pots in about 3 months from a rooted cutting.

*Cropping time to bloom*.—Approximately 20 months from time of rooting.

Stem description:

*Stem shape*.—Round.

*Stem color*.—144A.

*Stem size*.—Average of 8.2 cm in length, average of 2 mm in diameter.

*Stem surface*.—Slightly glossy.

*Stem aspect*.—Held strongly erect.

*Internode length*.—Average of 1.3 cm.

*Branching habit*.—Basal branching with lateral branching, about 32 lateral branches per 13 cm container.

Foliage description:

*Leaf shape*.—Narrowly ovate.

*Leaf division*.—Simple.

*Leaf base*.—Cuneate.

*Leaf apex*.—Acute, slightly more rounded.

*Leaf venation*.—Tri-nerved, leave aspect is concave in respect to the mid rib on the upper surface, mid rib is conspicuous, veins are a color between 139A and 141A on the upper and a color between 143B and 144A on the upper lower surface.

*Leaf margins*.—Entire.

*Leaf attachment*.—Sessile.

*Leaf arrangement*.—Opposite.

*Leaf surface*.—Upper and lower surface; glabrous, slightly shiny.

*Leaf color*.—Immature: upper; between 141A and 143A with a base of 143A, lower; between 143B and 144A. Mature: upper; between 139A and 141A (slightly darker), lower; between 143B and 144A.

*Leaf number*.—Average of 14 per stem per lateral branch.

*Leaf size*.—Average of 2.7 cm in length and 1 cm in width.

*Leaf substance*.—Thick, moderate to high durability to environmental stresses.

Flower description:

*Flower type*.—Axillary and terminal tubular flowers, axillary are solitary, terminal are solitary or in pairs.

*Flower fragrance*.—None.

*Flower lastingness*.—Average of 10 days on plant, persistent.

*Flower bud description*.—Narrowly oblong in shape, average of 3.5 cm in diameter and 8 mm in length, petal portion is 96A in color striped with 202A and calyx portion is 144C and 145A in color.

*Flower quantity*.—Average of 7 per stem.

*Flower aspect*.—Held upright.

*Flower shape*.—Tubular with 15% of flower opening near apex.

*Flower size*.—3.9 cm in depth, 1.7 cm in diameter.

*Peduncles*.—Not present.

*Pedicel description*.—Average of 4 mm in length and 1 mm in width, held at an angle of about 5° relative to stem, strong,144A in color.

*Petal description*.—5, narrowly oblong in shape, 85% of lower portion is fused into a tubular shape, margin is entire, apex is broadly acute, surface is smooth and slightly glossy in appearance.

*Petal size*.—About 3.9 cm in length and 9 mm in width.

*Petal color*.—Outer surface 96B striped with color between 97B and 202C (opening and fully open), inner surface 96B striped with 97C (opening and fully open), petals fade to 93A to 93B (both surfaces).

*Calyx form*.—Campanulate.

*Calyx size*.—Average of 1.8 cm in length and 1 cm in diameter.

*Sepal description*.—6 (average), linear in shape, margin is entire, apex is acute, base is cuneate and fused, surface is smooth and dull in appearance.

*Sepal size*.—Average of 1.8 cm in length, 3 mm in width.

*Sepal color*.—Outer and inner surface; 144C to 145A when opening and 144B to 144C with tips a color between 141B and 143A when mature.

Reproductive organs:

*Gynoecium*.—1 Pistil about 3 mm in length, stigma is decurrent and 150D in color, style is about 2 mm in length and 150D in color, ovary is 144A to 144B in color.

*Androceium*.—5 stamens, anthers are oblong in shape, basifixed, about 4 mm in length, 0.5 mm in width and 11A in color, filaments are about 2.3 mm in length and 145B to 145D in color, pollen is moderately abundant and 11B to 11C in color.

*Fruit*.—No fruit has been observed under the conditions tested.

I claim:

1. A new and distinct cultivar of *Gentiana* plant named 'Blue Rock' as herein illustrated and described.

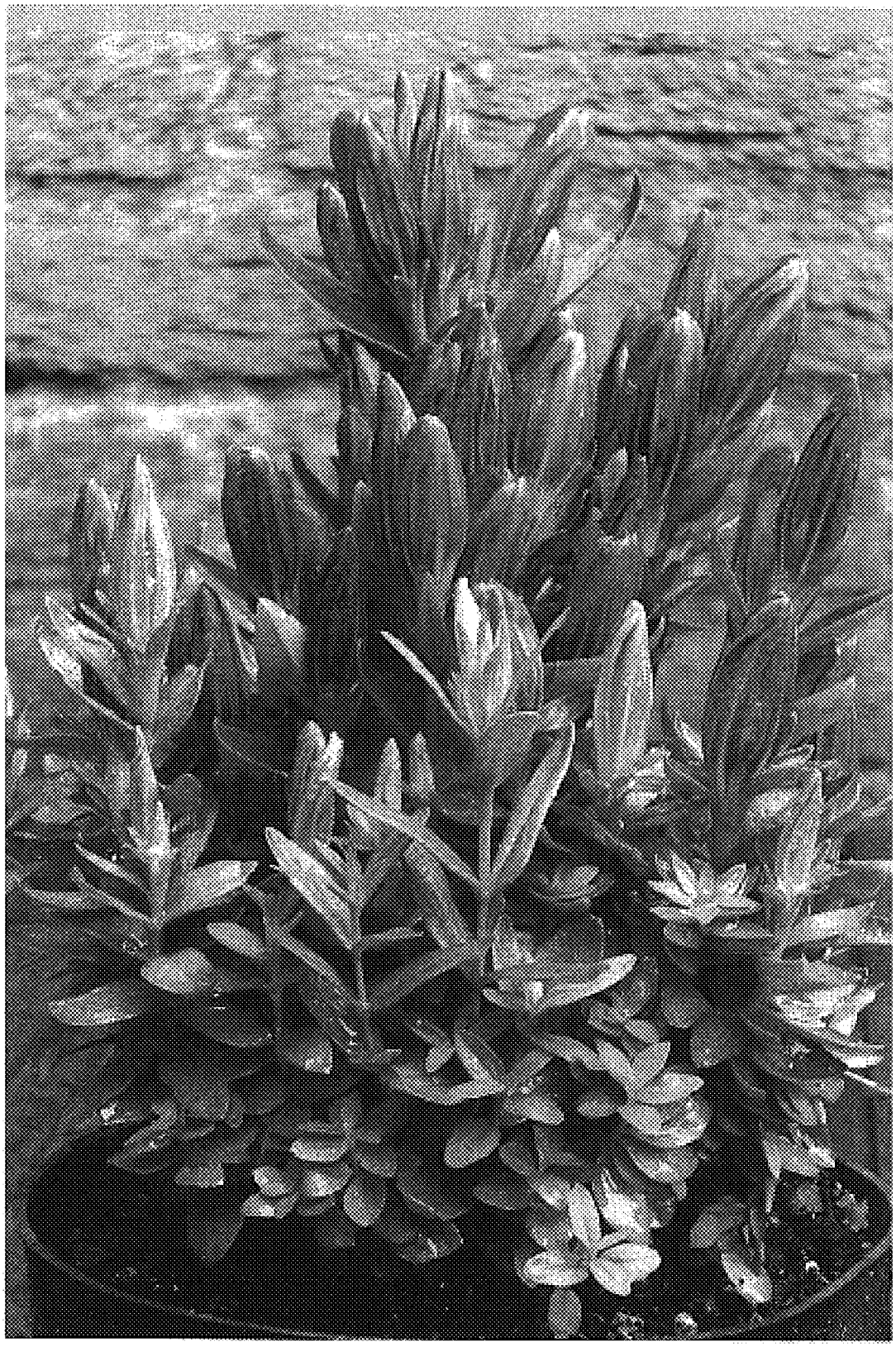

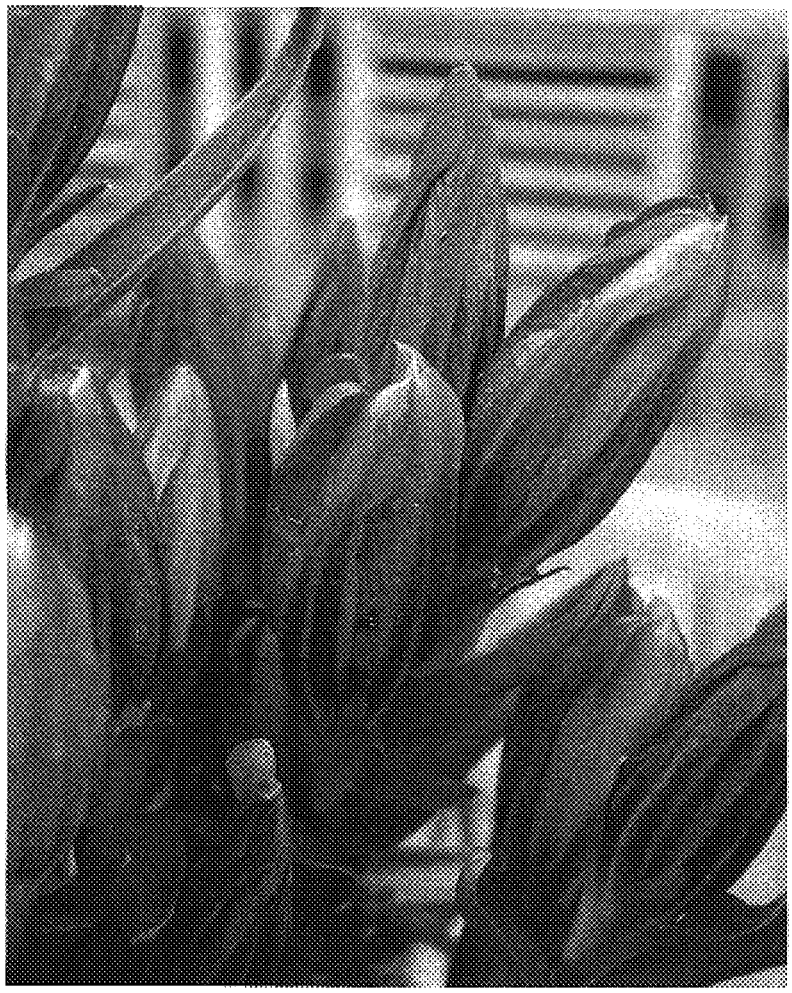
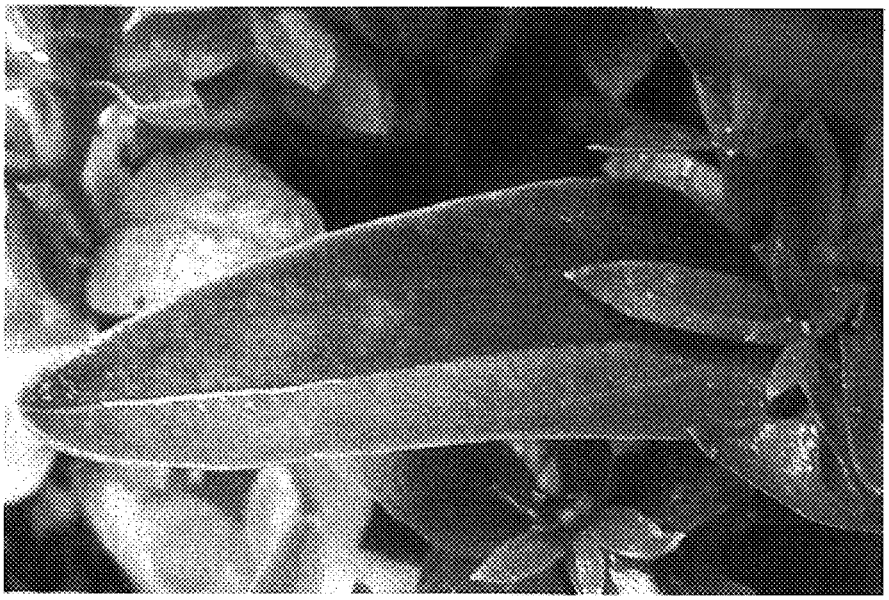

* * * * *